(12) United States Patent
Chu

(10) Patent No.: US 10,823,923 B2
(45) Date of Patent: Nov. 3, 2020

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/406,133

(22) Filed: May 8, 2019

(65) Prior Publication Data

US 2019/0346643 A1 Nov. 14, 2019

Related U.S. Application Data

(60) Provisional application No. 62/670,008, filed on May 11, 2018.

(51) Int. Cl.
  *G02B 6/44* (2006.01)
  *A61M 25/00* (2006.01)
  *A61B 18/26* (2006.01)

(52) U.S. Cl.
  CPC ......... *G02B 6/4439* (2013.01); *A61M 25/002* (2013.01); *A61B 18/26* (2013.01)

(58) Field of Classification Search
  None
  See application file for complete search history.

(56) References Cited

U.S. PATENT DOCUMENTS

| | | | |
|---|---|---|---|
| 9,173,710 | B2 | 11/2015 | Van Zuylen et al. |
| 2002/0130059 | A1 | 9/2002 | Armijo |
| 2002/0191938 | A1 | 12/2002 | Sheetz et al. |
| 2015/0094693 | A1 | 4/2015 | Suzuki et al. |
| 2016/0199079 | A1 | 7/2016 | Chu et al. |
| 2019/0154937 | A1 | 5/2019 | Chu et al. |

FOREIGN PATENT DOCUMENTS

| | | |
|---|---|---|
| EP | 3 228 252 A1 | 10/2017 |
| EP | 3 238 769 A1 | 11/2017 |

OTHER PUBLICATIONS

International Search Report and Written Opinion issued in International Application No. PCT/US2019/031242, dated Aug. 22, 2019 (14 pages).

*Primary Examiner* — Jerry Rahll
(74) *Attorney, Agent, or Firm* — Bookoff McAndrews, PLLC

(57) ABSTRACT

A medical system includes a tube and a plurality of clips that secure the tube in a partially spiral configuration. The medical system also includes a platform coupled to a radial exterior of the tube. The platform includes at least one hole and a plurality of retaining elements.

15 Claims, 7 Drawing Sheets

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/670,008, filed May 11, 2018, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for coupling a medical instrument to a storage, holding, or dispensing device to store, hold, dispense, or otherwise couple the medical instrument to the device.

BACKGROUND

Optical fibers or guidewires are used in a wide variety of medical procedures, including urology, neurology, otorhinolaryngology, ophthalmology, gastroenterology, cardiology, and gynecology. Generally, a user may deliver an optical fiber or a guidewire from a package, for example, in a spiral tube or loop configuration. However, as the optical fiber or guidewire is removed from the package to be delivered within a patient, the optical fiber or guidewire may inadvertently contact the floor or other surface in the operating room and become contaminated. Moreover, a user may remove the optical fiber or guidewire from the patient and wish to reuse the optical fiber or guidewire during the same medical procedure. However, there are additional risks of contamination or damage if the optical fiber or guidewire is not properly handled, coiled, or stored between uses. Additionally, the distal tip of the optical fiber or guidewire may be damaged if the optical fiber or guidewire is inserted back into the original packaging for temporary storage. The aforementioned contamination and damage risks may increase the cost, time, and necessary personnel for a medical procedure, further complicating and prolonging the procedure, and exposing the patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, a medical system may include a tube and a plurality of clips that secure the tube in a partially spiral configuration. The medical system also may include a platform coupled to a radial exterior of the tube. The platform may include at least one hole and a plurality of retaining elements.

The medical system may further include one or more of the following features. The platform may include at least one groove connecting to the interior of the tube. The at least one groove may extend in a curved angular pattern through at least a portion of the platform. The at least one groove may include two grooves, and the two grooves may be connected by a radially outward facing opening. The at least one hole may include a first hole and a second hole. The first hole may be positioned on one side of the radially outward facing opening, and the second hole may be positioned on the other side of the radially outward facing opening. The platform may include at least one arrow on one side of the radially outward facing opening.

A subset of the plurality of clips may couple the tube to the platform by engaging one or more slots in the platform. One of the clips in the subset may be coupled to one of the slots to enclose a portion of the groove, and the one of the clips may include a tab extending from an outer portion of the clip. The plurality of retaining elements each may include two L-shaped extensions separated by a gap. Each clip may include three partially cylindrical openings to receive and be coupled to the tube, and one or more of the clips may include an additional retaining element.

The medical system may further include an optical fiber having a proximal connector. A first portion of the optical fiber may be positioned within the tube, and a second portion of the optical fiber may be positioned within the groove. The medical system may further include a fiber clip connector. The fiber clip connector may be coupled to a portion of the tube and may include a connector slot positioned to the radial exterior of the tube and configured to receive the proximal connector. With the proximal connector positioned within the connector slot of the fiber clip connector, a distal tip of the optical fiber may be positioned within the tube. With the proximal connector disconnected from the slot of the fiber clip and positioned adjacent to the coupling of the platform and the tube, the distal tip of the optical fiber may extend out of the tube. The tube may be formed of a partially transparent extruded polymer.

In another example, a medical device may include a protective element configured to be coupled to one or more spiral or coiled devices. The protective element may include one or more slots to receive connections to the one or more spiral or coiled devices, one or more holes, at least one groove extending through the length of the protective element and sized to house one of the one or more spiral or coiled devices and including an outward facing opening, and a plurality of retaining elements.

The medical device may further include one or more of the following features. The protective element may be curved to span at least ninety degrees of a circle. The outward facing opening may be a radially outward facing opening. The at least one groove may include two grooves, and the two grooves may be connected by the radially outward facing opening. The one or more holes may include a first oval-shaped hole and a second oval-shaped hole. The first hole may be positioned on a first side of the radially outward facing opening, and the second hole may be positioned on a second side of the radially outward facing opening opposite to the first side. The plurality of retaining elements may include a first pair of retaining elements and a second pair of retaining elements. The first pair of retaining elements may be positioned on the first side, and the second pair of retaining elements may be positioned on the second side. One retaining element of each respective pair of retaining elements may be positioned on a first side of the groove, and the other retaining element of each respective pair of retaining elements may be positioned on a second side of the groove opposite to the first side of the groove.

In a further example, a medical system may include a tube, a plurality of clips that secure the tube in a partially spiral configuration, and a mounting element coupled to a radial exterior of the tube. The mounting element may include at least one hole and one or more retaining elements. The medical system may also include an optical fiber and a proximal connector. A first portion of the optical fiber may be positioned within the tube, and a second portion of the optical fiber may be positioned outside of the tube.

The medical system may further include one or more of the following features. The tube may include two skive holes in an outer portion of the partially spiral configuration, and the second portion of the optical fiber may be slidably secured to the tube in an area between the two skive holes by one of the plurality of clips. The mounting element may be a curved platform that includes two grooves, and the two grooves may be connected by a radially outward facing opening. The platform may further include a first oval-shaped hole and a second oval-shaped hole. The first hole may be positioned on a first side of the radially outward facing opening, and the second hole may be positioned on a second side of the radially outward facing opening opposite to the first side. The one or more retaining elements may include a first pair of retaining elements and a second pair of retaining elements. The first pair of retaining elements may be positioned on the first side, and the second pair of retaining elements may be positioned on the second side. Each retaining element of the respective pairs of retaining elements may be positioned on opposing sides of the groove.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems, devices, and methods to facilitate and improve the efficacy, efficiency, and safety of packaging, dispensing, and storing medical devices to be used during medical procedures. For example, aspects of the present disclosure may provide a user (e.g., a physician, medical technician, or other medical service provider) with the ability to more easily dispense and store an optical fiber, a guidewire, or other shaft-like medical element to be delivered within a patient and/or through an insertion device. Some aspects of the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
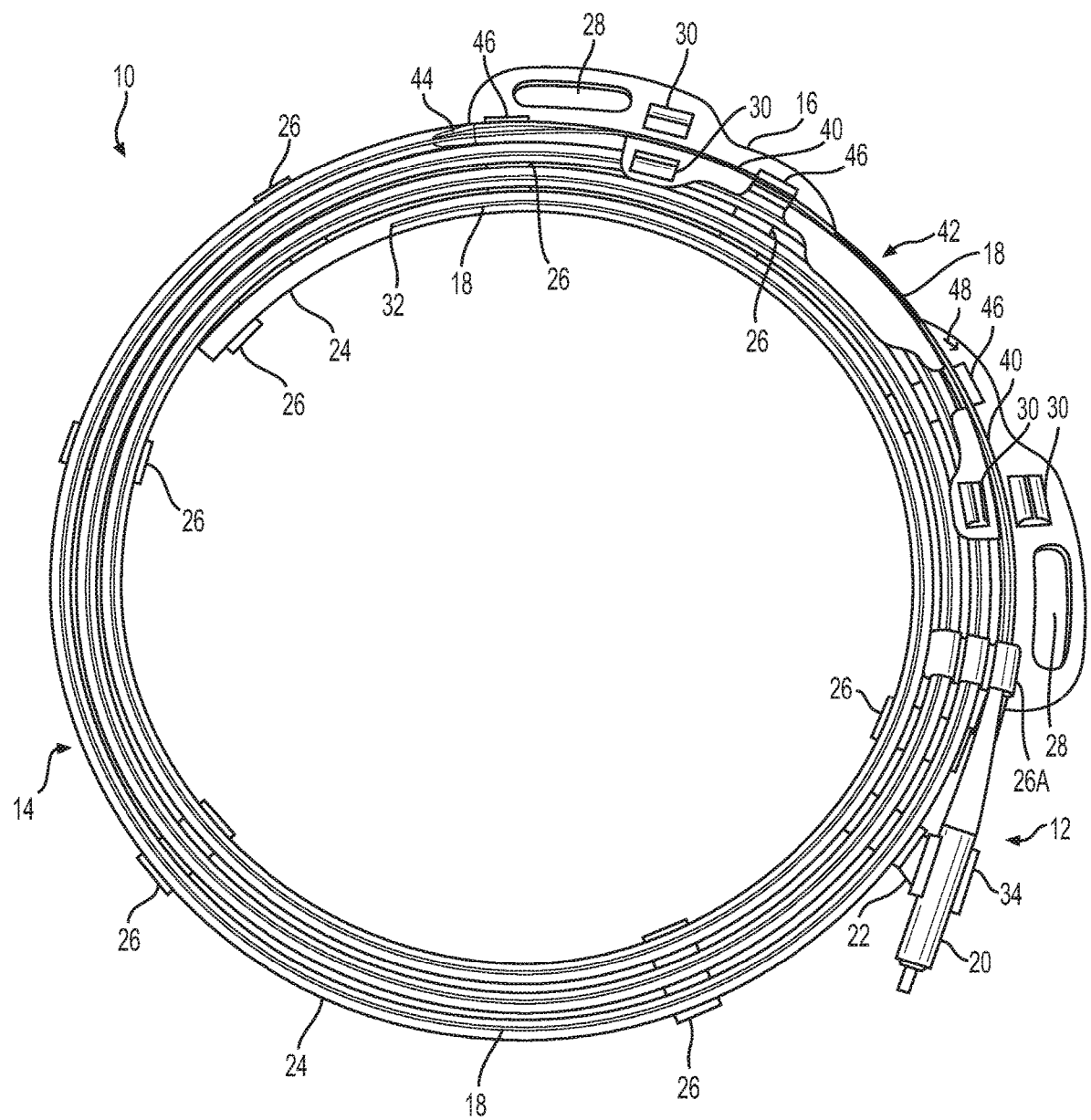
FIG. 1 illustrates a medical system, according to aspects of the present disclosure.

FIG. 1 illustrates a medical system 10 that includes an medical device 12, a storage loop 14, and a platform 16. Storage loop 14 and platform 16 may form a protective element to protect at least a portion of the medical device 12. Medical device 12 may include an optical fiber 18 and a proximal connector 20. A majority of optical fiber 18 may be removably stored within storage loop 14, and proximal connector 20 may be removably stored within a connector clip 22. Connector clip 22 may be coupled to storage tube 14 and extend in a radial direction from storage loop 14. Storage loop 14 may include a tube 24, and tube 24 may be held in a coil by one or more tube clips 26 to form storage loop 14. One or more tube clips 26 may also attach platform 16 to storage loop 14. Platform 16 may include one or more holes 28 to couple or mount platform 16 to an additional medical element. Platform 16 also includes one or more catches 30, and a portion or optical fiber 18 may be stored or secured within one or more catches 30 before, during, or between uses of optical fiber 18 after optical fiber 18 has been removed from storage loop 14.

Medical device 12 may include optical fiber 18 and proximal connector 20. Optical fiber 18 may include a width of approximately 100 microns, approximately 200 microns, approximately 500 microns, approximately 1000 microns, or larger. Optical fiber 18 includes a distal tip 32. When optical fiber 18 is positioned within storage loop 14 and proximal connector 20 is coupled to connector clip 22, distal tip 32 may be positioned within tube 24. Proximal connector 20 may be uncoupled from connector clip 22, and extended to an laser source (not shown) or other optical element. The extension of proximal connector 20 may help to unwind optical fiber 18 and remove at least a portion of optical fiber 18 from tube 24.

Although medical device 12 is discussed as including optical fiber 18, this disclosure is not so limited. In particular, medical device 12 may include a guidewire or another medical device that may be coiled and packaged within and then dispensed from storage loop 14 and temporarily stored using platform 16 of medical system 10.

Tube 24 may include a cylindrical cross-section with a hollow circular central opening. The inner diameter of tube 24 may be sized to receive optical fiber 18, with the inner diameter of tube 24 allowing optical fiber 18 to slide within tube 24. Tube 24 may be at least partially transparent, which may allow a user to observe the position of optical fiber 18 within tube 24. Tube 24 may be formed of an extruded polymer. Although storage loop 14 is shown as being a substantially circular spiral, this disclosure is not so limited. For example, tube 24 may be held in a substantially ovular spiral shape by tube clips 26 to form storage loop 14 in a different shape than that shown in FIG. 1.

One or more tube clips 26 may include partially cylindrical openings to receive different portions of tube 24 to secure tube 24 in the spiral or looped configuration, and/or to secure a portion of tube 24 to platform 16. For example, tube clips 26 may include three partially cylindrical grooves (FIG. 3) or may include four partially circular grooves (not shown) to securely receive or snap on to the outside diameter of tube 24. Medical system 10 may include two, four, six, eight, ten, or more tube clips 26 distributed around a circumference of storage loop 14. Medical system 10 may also include an even or odd number of tube clips 26. In one aspect, a first group or subset of tube clips 26 may secure various portions of tube 24 in the spiral or looped configuration. A second group or subset of tube clips 26 may secure platform 16 to storage loop 14. Another tube clip 26A may help to secure a portion of optical fiber 18 between storage loop 14 and platform 16, while also securing storage loop 14 and platform 16. As shown, tube clips 26 may be coupled to a back side of tube 24, and tube clip 26A may be coupled to a front side of tube 24. Tube clips 26 may also include one or more retaining elements, such as pivotable clamps, clips, or catches 30, to receive and temporarily store optical fiber 18. Connector clip 22 may include one or more grooves to receive or snap on to the outside diameter of tube 24 in a similar manner as tube clips 26. Connector clip 22 also includes a connector slot 34 extending away from tube 24 to receive a portion of proximal connector 20. In any of the above aspects, tube clips 26 or connector clip 22 may be formed of a molded or stamped polymer.

Figure 2:
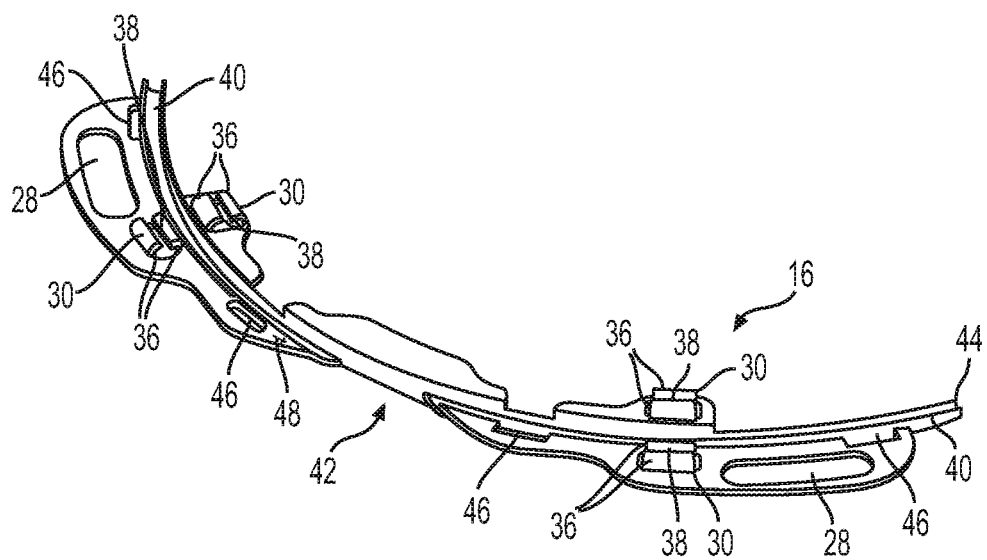
FIG. 2 illustrates a portion of the medical system of FIG. 1, according to aspects of the present disclosure.

As shown in FIGS. 1 and 2, platform 16 may form a partially circular element that spans approximately 90 degrees or more of the outer circumference of storage loop 14 to form the protective element. For example, although not shown, platform 16 may span approximately 110 degrees, 135 degrees, 180 degrees, 270 degrees, etc. of the outer circumference of storage loop 14. Platform 16 may include holes 28, for example, two holes 28 on opposing sides of platform 16. Holes 28 may be oval-shaped and may receive a hemostat, hanger, hook, or other securing element in order for medical system 10 to be coupled to a drape, a sheet, or other elevated element in an operating room.

As mentioned above, platform 16 may include one or more catches 30. For example, as shown in FIGS. 1 and 2, platform 16 may include four catches 30, with two pairs of catches 30 aligned along platform 16. Each catch 30 may include two extensions 36, for example L-shaped or J-shaped extensions, that extend away from platform 16 and are separated by a gap 38. Gap 38 is sized to be slightly wider than the diameter of optical fiber 18. As such, when optical fiber 18 is removed from tube 24, one or more portions of optical fiber 18 may be positioned within one or more catches 30 between extensions 36 of each catch 30 in order to temporarily store or loop optical fiber 18 between uses in a medical procedure. Optical fiber 18 may be removed from catches 30 by positioning optical fiber 18 within gap 38 of each catch 30, for example, in order to extend optical fiber 18 to deliver optical fiber 18 through an insertion device. Additionally, each catches 30 and extensions 36 may be different sizes to allow a user various options in which to position optical fiber 18.

Platform 16 may also include a groove 40 that extends through platform 16, and groove 40 may be substantially concentric with tube 24 of storage loop 14. Groove 40 may include a central opening 42 that is exposed radially outward. For example, groove 40 may include two grooves that open into central opening 42 on opposing sides of central opening 42. When medical device 12 is coupled to storage loop 14 and platform 16, a portion of optical fiber 18 may extend through groove 40 and be accessible to a user, for example, with a user's fingertips, via central opening 42. Platform 16 may further include a taper 44 couplable to an outer end of tube 24, and groove 40 may extend through taper 44. Taper 44 may be positioned within the outer end of tube 24 to help provide a smooth transition to optical fiber between tube 24 and groove 40. As such, when medical device 12 is coupled to platform 16, optical fiber 18 may extend from proximal connector 20 through groove 40, through taper 42, and within tube 24.

Furthermore, as shown in FIGS. 1 and 2, pairs of catches 30 may be positioned on opposing sides of central opening 42. For example, one pair of catches 30 may be positioned on a left side of central opening 42, and one pair of catches 30 may be positioned on a right side of central opening 42. Each catch 30 of a respective pair may be positioned on opposing sides of the groove 40. For example, one catch 30 may be positioned on a radially outer side of groove 40, and one catch 30 may be positioned on a radially inner side of groove 40.

As illustrated in FIGS. 1 and 2, platform 16 may further include one or more clip slots 46, which may receive portions of tube clips 26 to couple platform 16 to tube 24 of storage loop 14. Clip slots 46 may be positioned around platform 16, and may be radially outside of groove 40. In one aspect, platform 16 may include four clip slots 46, and tube clips 26 may be coupled to one or more portions of tube 24 and also through a respective clip slot 46. Alternatively, platform 16 may be coupled to storage loop 14 via another connection, for example, an adhesive. Optionally, platform 16 may also include one or more arrows 48 or other indicators to indicate to a user the direction to pull or slide optical fiber 18 in order to remove optical fiber 18 from tube 24. Platform 16 and the components thereon may be formed of a molded or stamped polymer.

Figure 3:
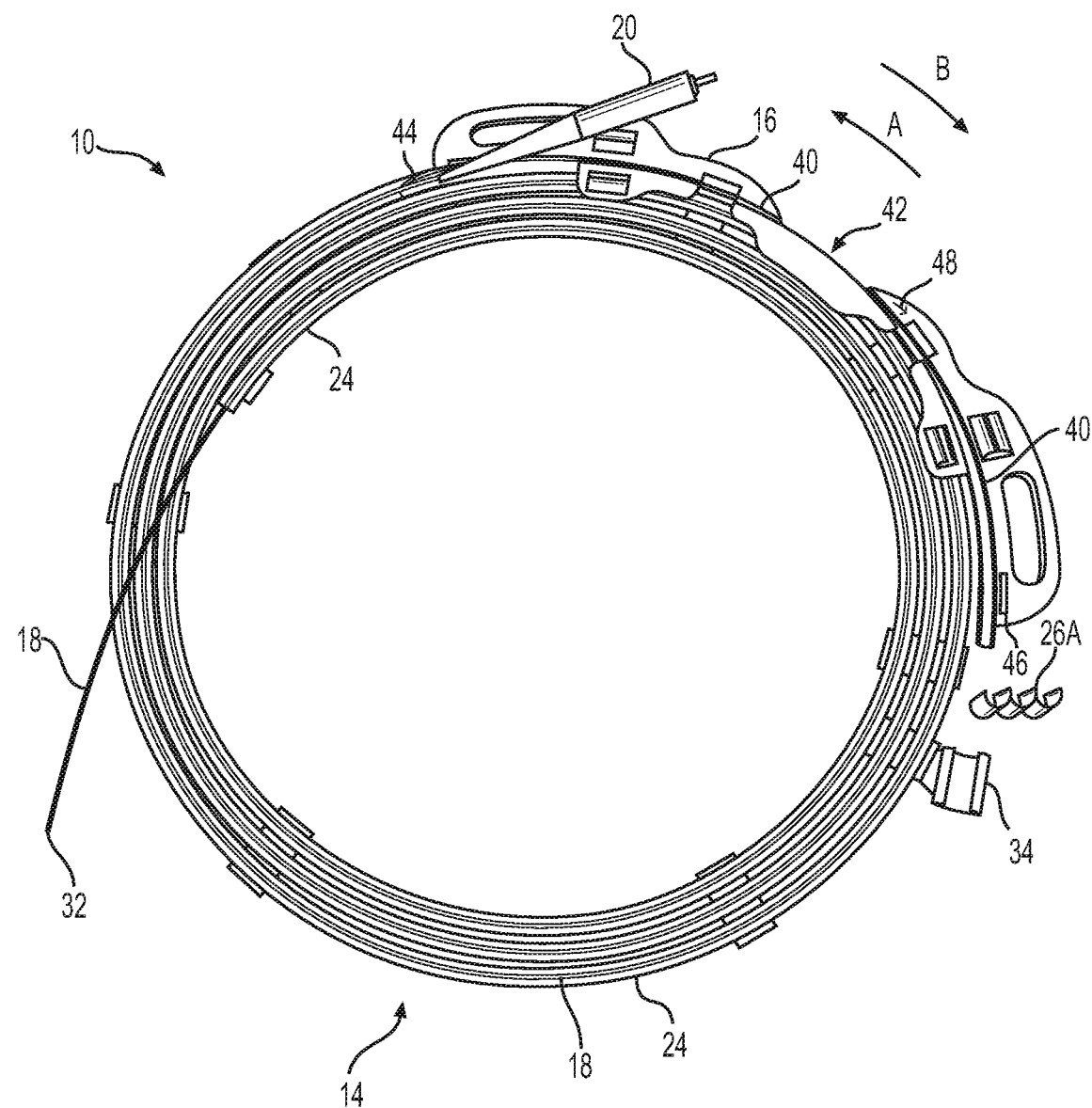
FIG. 3 illustrates another aspect of the medical system of FIG. 1, according to aspects of the present disclosure.

As shown in FIG. 3, proximal connector 20 may be disconnected from connector slot 34 and pushed or slid distally in direction A. With proximal connector 20 abutting or close to taper 44 and the connection of groove 40 to tube 24, distal tip 32 of optical fiber 18 may extend out of the distal or inner end of tube 24. In this example, tube clip 26A may be removed, and the portion of optical fiber 18 within groove 40 in FIG. 1 may be extended into tube 24. As such, a user may polish, clean, or otherwise treat distal tip 32 of optical fiber 18 before a medical procedure. In one aspect, a user may clean or polish a lens at distal tip 32 of optical fiber 18 before beginning the medical procedure. The user may then move proximal connector 20 in direction B to retract distal tip 32 within tube 24. The user may reposition proximal connector 20 within connector slot 34 and secure optical fiber 18 in groove 40 with tube clip 26A with distal tip 32 protected for later use.

Figure 4:
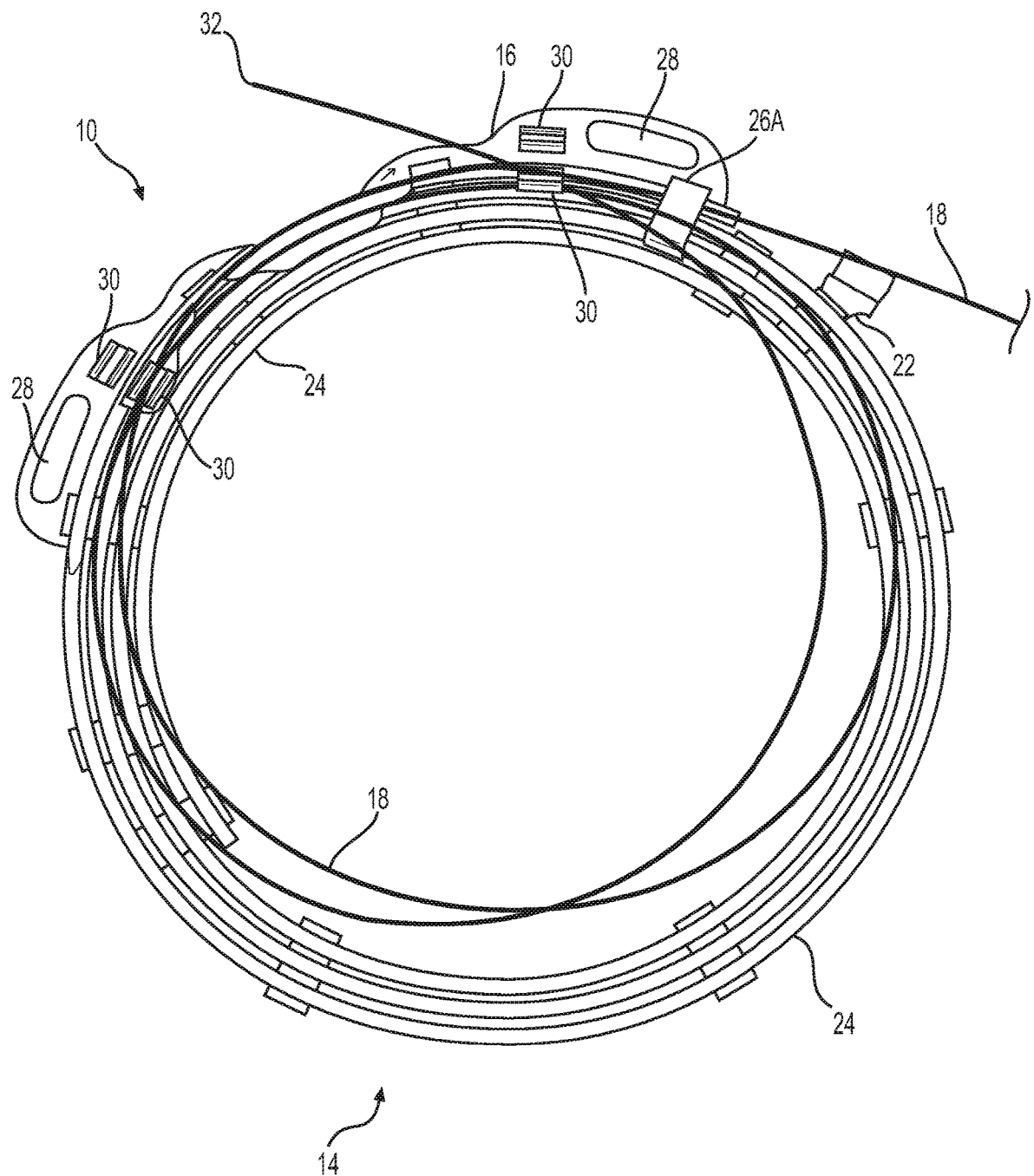
FIG. 4 illustrates a further aspect of the medical system of FIG. 1, according to aspects of the present disclosure.

Alternatively, the user may continue to move proximal connector 20 in direction B to extend proximal connector 20 and optical fiber 18 to a laser or other energy source (FIG. 4). The user may position optical fiber 18 within groove 40. The user may also secure optical fiber 18 to platform 16 by repositioning tube clip 26A to tube 24 and one clip slot 46 to partially enclose optical fiber 18 within groove 40. Optical fiber 18 unwinds from within tube 24 as proximal connector 20 is extended. As mentioned, tube 24 may be at least partially transparent, allowing the user to observe the amount of optical fiber 18 positioned within tube 24 during the extension. Moreover, it is noted that optical fiber 18 may include a length longer than a distance from the position of medical system 10 during the procedure to the energy source. As such, with proximal connector 20 extended and coupled to the energy source, a portion of optical fiber 18 may remain within tube 24. In this instance, the user may pinch or otherwise grasp the portion of optical fiber 18 exposed from groove 40 via central opening 42. The user may manipulate optical fiber 18 to remove distal tip 32 of optical fiber 18 from tube 24, for example, in the direction of arrow 48 or direction B. With distal tip 32 of optical fiber 18 removed from tube 24, the user may deliver the optical fiber through an insertion device and/or into the patient.

As shown in FIG. 4, optical fiber 18 may be fully dispensed from within tube 24. For example, optical fiber 18 may extend proximally for proximal connector 20 (not shown) to be connected to the energy source, and distal tip 32 may be removed from tube 24. Optical fiber 18 may be secured to platform 16 via tube clip 26A. Optical fiber 18 may be further secured to platform 16 via one or more catches 30. As shown, optical fiber 18 may form one or more loops when coupled to one or more catches 30. The rigidity, an outer coating, and/or other features or properties of optical fiber 18 may help to secure optical fiber 18 within catches 30 to form the one or more loops. While FIG. 4 illustrates the loops formed by optical fiber 18 having a smaller diameter than storage loop 14, this disclosure is not so limited, as the loops formed by optical fiber 18 may include a diameter larger than the diameter of storage loop 14.

Alternatively, rather than pinching a portion of optical fiber 18 exposed via central opening 42, the user may continue to move proximal connector 20 in direction B to withdraw the entirety of optical fiber 18 from tube 24. Optical fiber 18 may be delivered through an insertion device and/or into the patient, or the user may position one or more portions of optical fiber 18 within one or more catches 30 to temporarily loop or otherwise secure optical fiber 18 to platform 16.

With platform 16 coupled to a drape or other elevated element during a medical procedure, e.g., via a hemostat through one or more holes 28, optical fiber 18 may be temporarily secured to platform 16 via catches 30 to help ensure that optical fiber 18 does not contact the ground, obstruct the user's movements, or otherwise become contaminated or interfere with the procedure. Therefore, optical fiber 18 may be removed from tube 24 before being inserted through the insertion device and stored in a looped configuration before being inserted.

Alternatively or additionally, optical fiber 18 may be temporarily stored in the looped configuration after being inserted and removed from the patient, for example, during a ureteroscopic procedure with periodic or repeated lithotripsy. In one aspect, optical fiber 18 may be delivered to the patient's kidney, and laser energy may be applied to a kidney stone. Optical fiber 18 may be removed from the patient, and positioned in the looped configuration with catches 30 while the user performs another aspect of the procedure. Then, optical fiber 18 may again be delivered to the patient's kidney by uncoupling optical fiber 18 from catches 30. These steps may be repeated as many times as necessary during the procedure.

Figure 5:
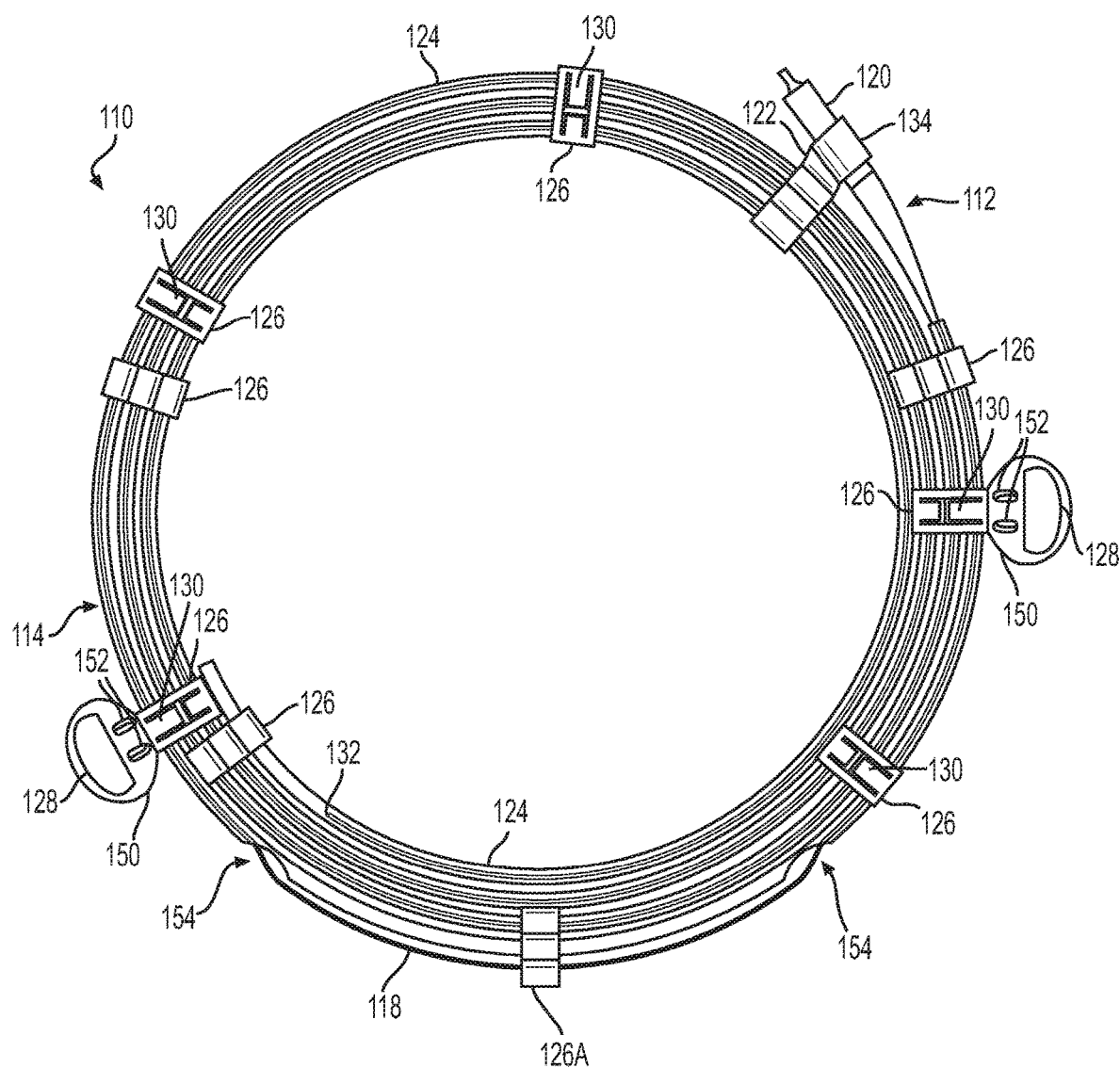
FIG. 5 illustrates an additional medical system, according to aspects of the present disclosure.

FIG. 5 illustrates an alternative example according to the present disclosure, with similar elements to medical systems 10 shown by 100 added to the reference numbers. Medical system 110 includes a medical device 112 and a storage loop 114. Medical device 112 includes an optical fiber 118 and a proximal connector 120. Storage loop 114 includes a tube 124 secured in a looped configuration by tube clips 126 to form a protective element. Tube clips 126 or a subset of tube clips 126 may include retaining elements, such as clamps, clips, or catches 130, on a surface opposite to tube 124. Alternatively, some tube clips 126 may include catches 130, and some tube clips 126 may include pivotable clips or clamping elements to optionally hold optical fiber 118 with greater security than catches 130. It is noted that FIG. 5 illustrates a view of a backside of medical system 110, such that moving proximal connector 120 counterclockwise extends optical fiber 118 proximally, rather than clockwise extension as shown in FIG. 1. Furthermore, tube clips 126 may be secured to tube 124 in different positions, with some tube clips 126 coupled to tube 124 on a front side, and some tube clips 126 coupled to tube 124 on a back side. As such, with tube clips 124 including catches 130, a user may optionally secure optical fiber 118 in a looped configuration to either the front or back side of medical system 110.

Medical system 110 also includes one or more mounting extensions 150. Mounting extensions 150 may be coupled to tube 124 with a tube clip 126 through a clip slot (not shown) in mounting extension 150. Alternatively, mounting extensions 150 may be integrally formed with a tube clip 126. Mounting extensions 150 include a hole 128 such that each mounting extension 150 may couple medical system 110 to a drape, sheet, or other elevated element during a medical procedure, for example, with a hemostat positioned through hole 128. Mounting extensions 150 may also include one or more fiber holes 152.

Tube 124 may include two or more skive holes 154 in an outer portion of storage loop 114. Optical fiber 118 may extend outside of tube 124 between skive holes 154. Optical fiber 118 may be coupled to tube 124 via one or more tube clips 126A. Alternatively, tube 124 may include one longer skive hole (not shown), and optical fiber 118 may be coupled to tube clip 126A exterior to tube 124 where exposed by the longer skive hole. In either example, tube clip 126A may include an outer cylindrical portion that is more fully closed than the other partial cylindrical openings of tube clips 126. For example, while tube clip 26A in FIG. 3 is shown as including three partially cylindrical openings to be clipped onto portions of tube 24 and into clip slot 46 to enclose optical fiber 18, tube clip 126A may include two partially cylindrical openings to be clipped onto portions of tube 124 and a third partially cylindrical opening that is almost fully cylindrical (e.g., with an opening approximately the same size as gap 38) to enclose optical fiber 118.

Optical fiber 118 may be coupled, uncoupled, and otherwise manipulated as discussed above with respect to medical system 10. For example, medical system 110 may be secured to a drape, sheet, or other elevated element via a hemostat through one of holes 128. Proximal connector 120 may be disconnected from connector slot 134 and extended proximally to an energy source. The portion of tube 124 between the proximalmost skive hole 154 and proximal connector 120 may also help to couple optical fiber 118 to tube 124. Optical fiber 118 may be pinched or grasped where exposed between skive holes 154 and removed from tube 124, with tube clip 126A securing a portion of optical fiber 118 to tube 124. Optical fiber 118 may then be stored in catches 130, or may be inserted into a patient. After insertion, optical fiber 118 may be removed and stored in a looped configuration within one or more catches 130 before being reinserted into the patient as many times as necessary during the procedure. Distal tip 132 may also optionally be positioned within one or more fiber holes 152 to secure or protect distal tip 132 and further ensuring that distal tip 132 or another portion of optical fiber 118 does not contact the floor or another surface of an operating room and become contaminated or damaged. For example, fiber holes 152 may be angled or tapered openings in which distal tip 132 may be positioned. Additionally, optical fiber 118 may be stored in one or more catches 130, with the various catches 130 providing various optional arrangements to loop and store optical fiber 118.

Figure 6:
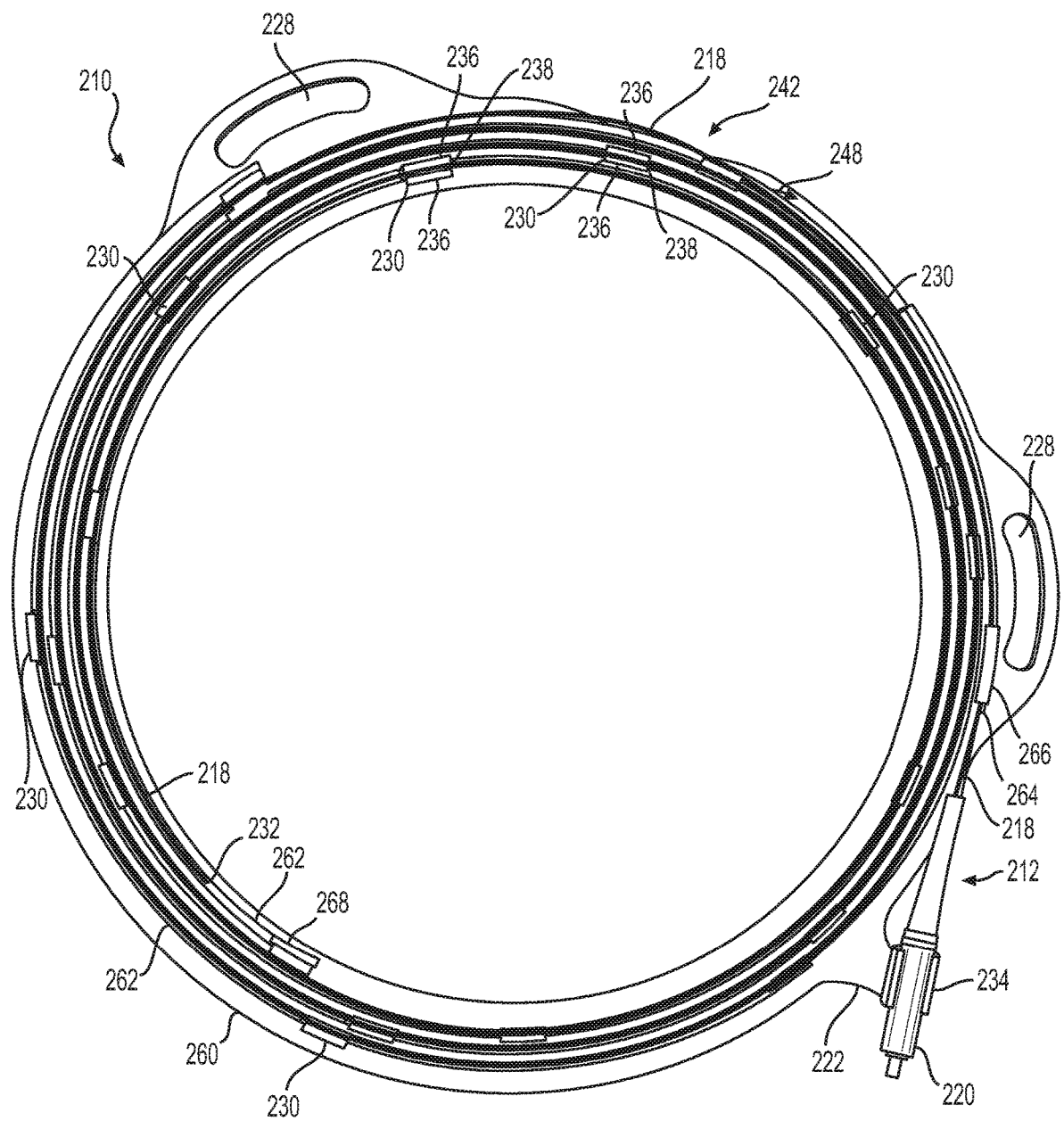
FIG. 6 illustrates an additional medical system, according to aspects of the present disclosure.

FIG. 6 illustrates an alternative example according to the present disclosure, with similar elements to medical systems 10 shown by 200 added to the reference numbers. Medical system 210 includes a medical device 212 and a combination element 260. Medical device 212 may be an optical fiber 218 and a proximal connector 220.

Combination element 260 may be a single element and may be formed of molded material, such as, for example, a plastic or polymer. Combination element 260 includes a spiral groove 262, for example, in a shape similar to storage loop 14, and may form a protective element. Groove 262 may temporarily store a portion of optical fiber 218. Combination element 260 may include a connector clip 222 with a connector slot 234, which may temporarily receive or store proximal connector 220. Combination element 260 may also include one or more holes 228, which may receive a hemostat or other clip to secure combination element 260 to a drape, sheet, or other elevated element.

Combination element 260 may include one or more catches 230, which may be positioned on combination element 260 radially inward of groove 262. Alternatively or additionally, combination element 260 may include one or more catches 230 that are positioned around or partially span portions of groove 262. For example, one or more catches 230 may include two extensions 236 separated by a gap 238. Extensions 236 may extend from combination element 260 away from groove 262, and/or may be partially span or narrow groove 262. Alternatively, spiral groove 262 may include one or more windows or wider openings, and one or more catches 230 may include an angled extension that spans or narrows a portion of the window to form a gap. The gap formed by the portion of window not spanned by the angled extension may be curved, s-shaped, straight, or any other appropriate shape.

Combination element 260 may further include a central opening 242, and a radial outermost portion of groove 262 may open into central opening 242, allowing a user to pinch, grasp, or otherwise access a portion of optical fiber 218 exposed in central opening 242. A portion of spiral groove 262 extending between central opening 242 and an outer opening 264 may be closed to form a closed portion 266. Closed portion 266 may help to secure a portion of optical fiber 218 within spiral groove 262 proximal of central opening 242 when optical fiber 218 is fully extended from spiral groove 262. Moreover, combination element 260 may include an arrow 248 to indicate to a user a direction in which to manipulate optical fiber 218 in order to extend optical fiber 218 from spiral groove 262. Furthermore, although not shown, combination element 260 may include one or more windows in a rear side to allow access for one or more tools or other elements into spiral groove 262.

Combination element 260 may include an inner opening 268 that extends to an inner portion of spiral groove 262. As such, a user may disconnect proximal connector from connector slot 34 and extend a distal tip 232 of optical fiber 218 out of inner opening 268 for cleaning, polishing, or other treatment, as discussed above. Additionally, the user may extend optical fiber 218 and proximal connector 220 proximally, for example, in the direction of arrow 248, to couple medical device 212 to an energy source. The user may also access the portion of optical fiber 218 exposed via central opening 242. The user may remove the distal portion of optical fiber 218, which may then be extended into an insertion device and/or into a patient. Additionally, optical fiber 218 may be stored in one or more catches 230, with the various catches 230 providing various arrangements to loop and store optical fiber 218, either before or between insertions during the medical procedure.

Figure 7:
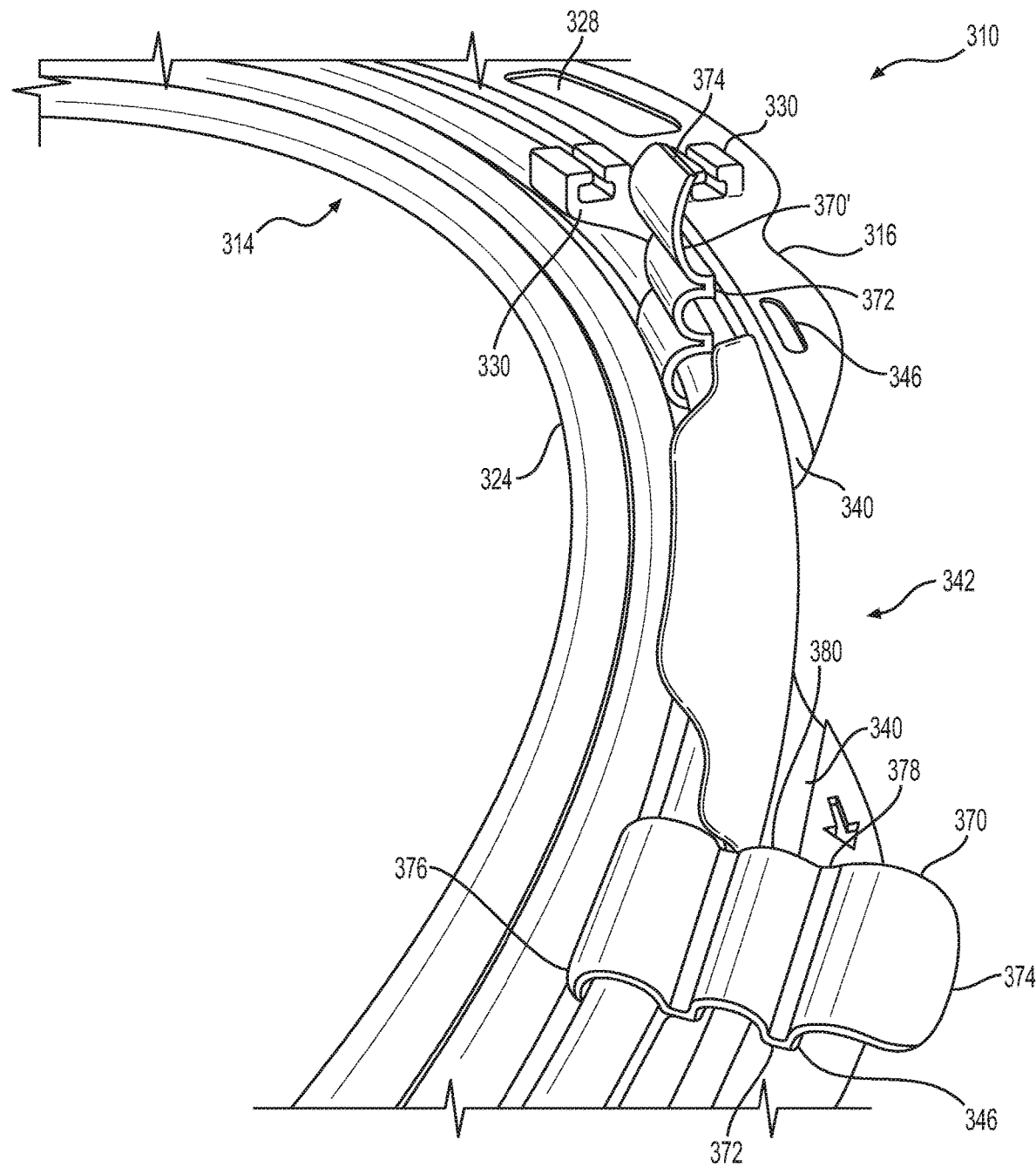
FIG. 7 illustrates an additional aspect that may be incorporated in any of the aforementioned medical systems, according to aspects of the present disclosure.

FIG. 7 illustrates a portion of an alternative medical system according to the present disclosure, with similar elements to medical system 10 shown by 300 added to the reference numbers. Medical system 310 includes a medical device (not shown) and a storage loop 314 coupled to a platform 316. The medical device may be an optical fiber and a proximal connector, as discussed above. Storage loop 314 includes a tube 324 secured in a looped configuration by one or more tube clips (not shown), as discussed with respect to FIGS. 1-6, to form a protective element to help protect at least a portion of the optical fiber or the proximal connector. Additionally, medical system 310 may include one more pivot clips 370. It is noted that the aspects of FIG. 7, including pivot clips 370, may be incorporated in any of the medical systems described above.

In one aspect, platform 316 may include clips slots 346 on one or both sides of central opening 342, along with holes 328 and catches 330 as discussed above. Pivot clips 370 may include a slot extension 372 and a tab 374. As such, an inner portion 376 of pivot clip 370 may be coupled to a portion of tube 324, and an outer portion 378 of pivot clip 370 may be secured to platform 316 via clip slot 346. A central portion 380 of pivot clip 370 may span and partially enclose groove 340 to help secure a portion of the optical fiber (not shown) within groove 340 and to platform 316. Furthermore, a user may actuate pivot clip 370 by gripping and/or applying force to tab 374 to pivot outer portion 378 away from platform 316 and move slot extension 372 out of clip slot 346. As such, pivot clip 370 may remain at least partially connected to tube 324, with the connection acting as a hinge, while not enclosing groove 340, as shown with respect to tube clip 370' in FIG. 7. Pivot clip 370 may allow a user to selectively secure the optical fiber or the proximal connector within a portion of groove 340 or to platform 316 without pinching or clamping the optical fiber or the proximal connector. It is also noted that a portion of groove 340, for example, the proximal portion, may be wider than another portion of groove 340, for example, the distal portion. As such, a portion of the proximal connector may be at least partially positioned within the wider portion of groove 340 and secured within groove 340 via pivot clip 370. Additionally, pivot clip 370 may be used with any of the medical systems 10, 110, and 210 discussed above to secure a portion of the optical fiber or proximal connector within the groove or to the platform.

The systems, devices, and methods discussed herein may help to allow a user to package, dispense, and store optical fiber 18, 118, 218 or other coiled element to be used during a medical procedure. As discussed, optical fiber 18, 118, 218 may be removed from tube 24, 124, 324, or spiral groove 262 and coupled to catches 30, 130, 230, 330 on platform 16, 316, tube clips 26, 126, mounting extensions 150, or combination element 260 in a looped configuration. Then, with system 10, 110, 210, 310 coupled to a drape, sheet, or other elevated element in the operating room, a user may help to ensure that optical fiber 18, 118, 218 does not contact the ground or other surfaces. Optical fiber 18, 118, 218 may also be re-coupled to catches 30, 130, 230, 330 during intermediate steps in the same operation. As such, system 10, 110, 210, 310 may help to reduce the risk of contamination of optical fiber 18, 118, 218 while also reducing the likelihood of optical fiber 18, 118, 218 interfering with the intermediate steps of the procedure since optical fiber 18, 118, 218 may be temporarily coiled and positioned in an auxiliary position when not in use. Moreover, extensions 36, 236 may help to reduce the likelihood of damage to optical fiber 18, 118, 218 by providing for a secure coupling of optical fiber 18, 118, 218 to platform 16, 316, tube clips 26, 126, mounting extensions 150, or combination element 260 without compressing optical fiber 18, 118, 218.

Medical systems 10, 110, 210 and 310 are also selectively couplable or positionable to different medical elements and in different configurations. For example, if medical system 10, 110, 210, 310 is used in a ureteroscopic procedure, platform 16, 316, mounting extension 150, or combination element 260 may be clipped to a sheet or drape at a position near either the patient's left or right knee by positioning a hemostat through one of holes 28, 128, 228, 328. In one aspect, platform 16, 316, mounting extension 150, or combination element 260 may be secured to a drape near the patient's left knee, and the hemostat may be positioned through hole 28, 128, 228, 328 on the right side of central opening 42, 242, 342 or skive holes 154. In another aspect, platform 16, 316, mounting extension 150, or combination element 260 may be secured to a drape near the patient right knee, and the hemostat may be positioned through hole 28, 128, 228, 328 on the left side of central opening 42, 242, 342 or skive holes 154.

In any of the above examples, platform 16, 316, tube clips 26, 126, mounting extensions 150, and combination element 260 may provide a user with the ability to use optical fiber 18, 118, 218 or another coiled element that is prepackaged in tube 24, 124, 324 or spiral groove 262. Tube clips 26, 126 may secure tube 24, 124, 324 in a partially coiled configuration to form storage loop 14, 114, 314 and also secure platform 16, 316 or mounting extensions 150 to storage loop 14, 114, 314. Moreover, combination element 260 is a single element, and may be prepackaged with different sized optical fibers 218, a guidewire, or other spiral elements within spiral groove 262. As discussed with respect to FIGS. 3, 4, 6, and 7 proximal connector 20, 120, 220 may be uncoupled from connector clip 22, 122, 222 or pivot clip 370. Proximal connector 20, 120, 220 may allow the user either to extend distal tip 32, 132, 232 distally out of the inner end of tube 24, 124, 324 or inner opening 268 so the user may clean, polish, or treat distal tip 32, 132, 232, or to retract optical fiber 18, 118, 218 proximally out of the outer end of tube 24, 124, 324 or combination element 260 such that distal tip 32, 132, 232 may be delivered to the patient. Furthermore, the connection of optical fiber 18, 118 to tube clip 26A, 126A, pivot clip 370, and the closed portion 266 of combination element 260 may help to ensure that optical fiber 18, 118, 218 remains connected to storage loop 14, 114, 314 or combination element 260 during the procedure. The systems, devices, and methods disclosed herein may help to reduce the duration and number of medical professionals or medical instruments necessary during the medical procedure.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical system, comprising:
   a tube;
   a plurality of clips that secure the tube in a partially spiral configuration; and
   a platform coupled to a radial exterior of the tube, wherein the platform includes at least one hole and a plurality of retaining elements,
   wherein the platform includes at least two grooves extending in a curved angular pattern through at least a portion of the platform, wherein at least one groove connects to the interior of the tube, and wherein the two grooves are connected by a radially outward facing opening.

2. The medical system of claim 1, wherein the at least one hole includes a first hole and a second hole, and wherein the first hole is positioned on one side of the radially outward facing opening, and wherein the second hole is positioned on the other side of the radially outward facing opening.

3. The medical system of claim 2, wherein the platform includes at least one arrow on one side of the radially outward facing opening.

4. The medical system of claim 3, wherein a subset of the plurality of clips couple the tube to the platform by engaging one or more slots in the platform.

5. The medical system of claim 4, wherein one of the clips in the subset is coupled to one of the slots to enclose a portion of the groove, and wherein the one of the clips includes a tab extending from an outer portion of the clip.

6. The medical system of claim 1, wherein the plurality of retaining elements each include two L-shaped extensions separated by a gap.

7. The medical system of claim 1, wherein each clip includes three partially cylindrical openings to receive and be coupled to the tube, and
   wherein one or more of the clips includes an additional retaining element.

8. The medical system of claim 1, further including an optical fiber having a proximal connector, wherein a first portion of the optical fiber is positioned within the tube, and wherein a second portion of the optical fiber is positioned within the groove.

9. The medical system of claim 8, further including a fiber clip connector, wherein the fiber clip connector is coupled to a portion of the tube and includes a connector slot positioned to the radial exterior of the tube and configured to receive the proximal connector.

10. The medical system of claim 9, wherein with the proximal connector positioned within the connector slot of the fiber clip connector, a distal tip of the optical fiber is positioned within the tube, and wherein with the proximal connector disconnected from the slot of the fiber clip and positioned adjacent to the coupling of the platform and the tube, the distal tip of the optical fiber extends out of the tube.

11. The medical system of claim 1, wherein the tube is formed of a partially transparent extruded polymer.

12. A medical device, comprising:
a protective element configured to be coupled to one or more spiral or coiled devices, wherein the protective element includes:
one or more slots to receive connections to the one or more spiral or coiled devices;
one or more holes;
at least two grooves extending through portions of the length of the protective element and sized to house one of the one or more spiral or coiled devices and including a radially outward facing opening; and
a plurality of retaining elements,
wherein the protective element is curved to span at least ninety degrees of a circle, and wherein the two grooves are connected by the radially outward facing opening.

13. The medical device of claim 12, wherein the one or more holes includes a first oval shaped hole and a second oval shaped hole, and wherein the first hole is positioned on a first side of the radially outward facing opening, and wherein the second hole is positioned on a second side of the radially outward facing opening opposite to the first side; and
wherein the plurality of retaining elements includes a first pair of retaining elements and a second pair of retaining elements, wherein the first pair of retaining elements is positioned on the first side, wherein the second pair of retaining elements is positioned on the second side, wherein one retaining element of each respective pair of retaining elements is positioned on a first side of the groove, and wherein the other retaining element of each respective pair of retaining elements is positioned on a second side of the groove opposite to the first side of the groove.

14. A medical system comprising:
a tube;
a plurality of clips that secure the tube in a partially spiral configuration;
a mounting element coupled to a radial exterior of the tube, wherein the mounting element includes at least one hole and one or more retaining elements; and
an optical fiber and a proximal connector, wherein a first portion of the optical fiber is positioned within the tube, and wherein a second portion of the optical fiber is positioned outside of the tube,
wherein the tube includes two skive holes in an outer portion of the partially spiral configuration, and wherein the second portion of the optical fiber is slidably secured to the tube in an area between the two skive holes by one of the plurality of clips.

15. The medical system of claim 14, wherein the mounting element is a curved platform that includes two grooves, and wherein the two grooves are connected by a radially outward facing opening;
wherein the platform further includes a first oval shaped hole and a second oval shaped hole, and wherein the first hole is positioned on a first side of the radially outward facing opening, and wherein the second hole is positioned on a second side of the radially outward facing opening opposite to the first side; and
wherein the one or more retaining elements includes a first pair of retaining elements and a second pair of retaining elements, wherein the first pair of retaining elements is positioned on the first side, wherein the second pair of retaining elements is positioned on the second side, and wherein each retaining element of the respective pairs of retaining elements are positioned on opposing sides of the groove.

* * * * *